(12) United States Patent
Mou et al.

(10) Patent No.: US 11,353,438 B2
(45) Date of Patent: Jun. 7, 2022

(54) GAS DETECTING MODULE

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Chang-Yen Tsai, Hsinchu (TW); Wei-Ming Lee, Hsinchu (TW); Chun-Yi Kuo, Hsinchu (TW); Tsung-I Lin, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 0 days.

(21) Appl. No.: 17/017,025

(22) Filed: Sep. 10, 2020

(65) Prior Publication Data

US 2021/0109073 A1 Apr. 15, 2021

(30) Foreign Application Priority Data

Oct. 9, 2019 (TW) ................................ 108136741

(51) Int. Cl.
  *G01N 33/00* (2006.01)
  *G01N 1/24* (2006.01)
(52) U.S. Cl.
  CPC .......... *G01N 33/0047* (2013.01); *G01N 1/24* (2013.01); *G01N 33/0009* (2013.01); *G01N 33/0011* (2013.01); *G01N 33/0016* (2013.01); *G01N 33/0031* (2013.01)
(58) Field of Classification Search
  CPC .. G01N 33/0047; G01N 1/24; G01N 33/0009; G01N 33/0011; G01N 33/0031; G01N 33/0016

USPC ......................................................... 73/23.2
See application file for complete search history.

(56) References Cited

U.S. PATENT DOCUMENTS

| | | | | |
|---|---|---|---|---|
| 8,499,613 B2* | 8/2013 | Ziglioli | ............. | G01N 33/0009 73/23.34 |
| 9,074,731 B2* | 7/2015 | Barrett | ...................... | F17D 1/00 |
| 9,310,363 B2* | 4/2016 | Shachar | ............ | G01N 33/5438 |
| 9,910,021 B2* | 3/2018 | Chang | .................. | G01N 1/4044 |
| 10,161,835 B1* | 12/2018 | Moorman | ................ | G01N 1/14 |
| 10,488,305 B2* | 11/2019 | Miller-Lionberg | ........................ | G01N 1/2273 |

(Continued)

FOREIGN PATENT DOCUMENTS

| CN | M562892 | * | 7/2018 | ............ F04B 45/047 |
| TW | M562892 U | | 7/2018 | |

(Continued)

*Primary Examiner* — Clayton E. LaBalle
*Assistant Examiner* — Kevin C Butler
(74) *Attorney, Agent, or Firm* — Birch, Stewart, Kolasch & Birch, LLP

(57) ABSTRACT

A gas detecting module is disclosed. A gas-inlet concave and a gas-outlet concave are formed on a sidewall of a base. A gas-inlet-groove region and a gas-outlet-groove region are formed on a surface of the base. The gas-inlet concave is in fluid communication with a gas-inlet groove of the gas-inlet-groove region, and the gas-outlet concave is in fluid communication a gas-outlet groove of the gas-outlet-groove region. The gas-inlet-groove region and the gas-outlet-groove region are covered by a thin film to achieve the effectiveness of laterally inhaling and discharging out gas relative to the gas detecting module.

4 Claims, 20 Drawing Sheets

(56) References Cited

U.S. PATENT DOCUMENTS

| | | | | |
|---|---|---|---|---|
| 2003/0159495 | A1* | 8/2003 | Cardinale | G01N 1/24 |
| | | | | 73/23.2 |
| 2014/0347663 | A1* | 11/2014 | Rodes | G01N 33/0016 |
| | | | | 356/338 |
| 2016/0187214 | A1* | 6/2016 | Al-Hemyari | G01N 33/0016 |
| | | | | 73/31.04 |
| 2017/0133212 | A1* | 5/2017 | Mensa | G01N 33/0016 |
| 2017/0189882 | A1* | 7/2017 | Eisele | B01J 15/00 |
| 2017/0241963 | A1* | 8/2017 | Richter | G01N 33/0031 |
| 2017/0276627 | A1* | 9/2017 | Dobrokhotov | G01N 33/0031 |
| 2019/0033177 | A1* | 1/2019 | Mou | F04D 33/00 |
| 2020/0003741 | A1* | 1/2020 | Buck | G01N 1/4022 |
| 2020/0116691 | A1* | 4/2020 | Maffei | A61B 5/097 |
| 2020/0277948 | A1* | 9/2020 | Kutter | F04B 43/046 |
| 2020/0292437 | A1* | 9/2020 | Mou | G01N 15/06 |
| 2021/0010972 | A1* | 1/2021 | Dobrokhotov | G01N 27/4146 |
| 2021/0190646 | A1* | 6/2021 | Volckens | G01N 1/2205 |

FOREIGN PATENT DOCUMENTS

| | | |
|---|---|---|
| TW | M570950 U | 12/2018 |
| TW | M574231 U | 2/2019 |
| TW | M582134 U | 8/2019 |

* cited by examiner

GAS DETECTING MODULE

FIELD OF THE INVENTION

The present disclosure relates to a gas detecting module, and more particularly to an extremely thin gas detecting module which is used to integrate with a portable electronic device or a mobile device.

BACKGROUND OF THE INVENTION

In recent years, people's requirements for the quality of the living environment have gradually increased. Before going out, people are paying more and more attention to the air quality in addition to the weather information. However, the conventional air quality information can only be obtained from the monitoring stations set up by the Environmental Protection Administration of the Executive Yuan, and the monitoring stations can only provide the air quality information about a large area rather than a small area.

Therefore, there is a need to provide a gas detecting module capable of being integrated with a portable electronic device. In this way, people can easily obtain the air quality information through the portable electronic device.

SUMMARY OF THE INVENTION

An object of the present disclosure provides a gas detecting module including a base, a micro pump, a driving circuit board and a gas sensor collaborated to form a modular structure, which can be easily embedded in a mobile device or a portable electronic device for application.

In accordance with an aspect of the present disclosure, a gas detecting module is provided. The gas detecting module includes a base, a micro pump, a driving circuit board, a gas sensor and a thin film. The base includes a first substrate, a second surface, a plurality of sidewalls, an accommodating space, a gas-inlet-groove region and a gas-outlet-groove region. The second surface is opposite to the first surface. The plurality of sidewalls is extending longitudinally from the perimeter of the first surface to the perimeter of the second surface. One of the sidewalls has a gas-inlet concave and a gas-outlet concave recessed therefrom, and the gas-inlet concave and the gas-outlet concave are spaced apart. The accommodating space is recessed from the second surface toward the first surface and located in an inner space defined by the plurality of sidewalls, and the accommodating space is divided into a micro-pump-loading region, a detection region and a gas-flowing-path region. The micro-pump-loading region and the gas-flowing-path region are in communication with each other through a venting hole, and the detection region and the gas-flowing-path region are in communication with each other through a communicating opening. The gas-inlet-groove region is recessed on the first surface and includes a gas-inlet aperture and a gas-inlet groove. The gas-inlet aperture is in communication with the gas-flowing-path region, and the gas-inlet groove is in communication with the gas-inlet concave of the sidewall. The gas-outlet-groove region is recessed on the first surface and includes a gas-outlet aperture and a gas-outlet groove. The gas-outlet aperture is in communication with the micro-pump-loading region, and the gas-outlet groove is in communication with the gas-outlet concave of the sidewall. The micro pump is accommodated within the micro-pump-loading region and covers the gas-outlet aperture. The driving circuit board covers and is attached to the second surface of the base to form the micro-pump-loading region, the detection region, and the gas-flowing-path region of the accommodating space. Gas is inhaled through the gas-inlet aperture of the gas-inlet-groove region and discharged out through the gas-outlet aperture of the gas-outlet-groove region to form a gas flowing path. The gas sensor is disposed on and electrically connected to the driving circuit board and accommodated within the detection region to detect the gas flowing therethrough. The thin film covers and is attached to the gas-inlet-groove region and the gas-outlet-groove region. The gas is laterally inhaled through the gas-inlet concave of the sidewall, flows into the gas-inlet-groove region through the gas-inlet groove, then flows into the gas flowing path through the gas-inlet aperture, and is discharged out through the gas-outlet aperture of the gas-outlet-groove region, so that the gas is laterally discharged out the gas detecting module through the connection of the gas-outlet concave of the sidewall to the gas-outlet groove of the gas-outlet-groove region. A length of the gas detecting module ranges from 2 mm to 4 mm, a width of the gas detecting module ranges from 2 mm to 4 mm, and a thickness of the gas detecting module ranges from 1 mm to 3.5 mm. The micro pump accelerates the flow of the gas, and the gas is laterally inhaled relative to the gas detecting module into the gas-flowing-path region through the gas-outlet concave of the sidewall, flows into the detection region to be detected, and is discharged out through the gas-outlet aperture of the gas-outlet-groove region by the micro pump, so that the gas is laterally discharged out the gas detecting module through the connection of the gas-outlet concave of the sidewall to the gas-outlet groove of the gas-outlet-groove region.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
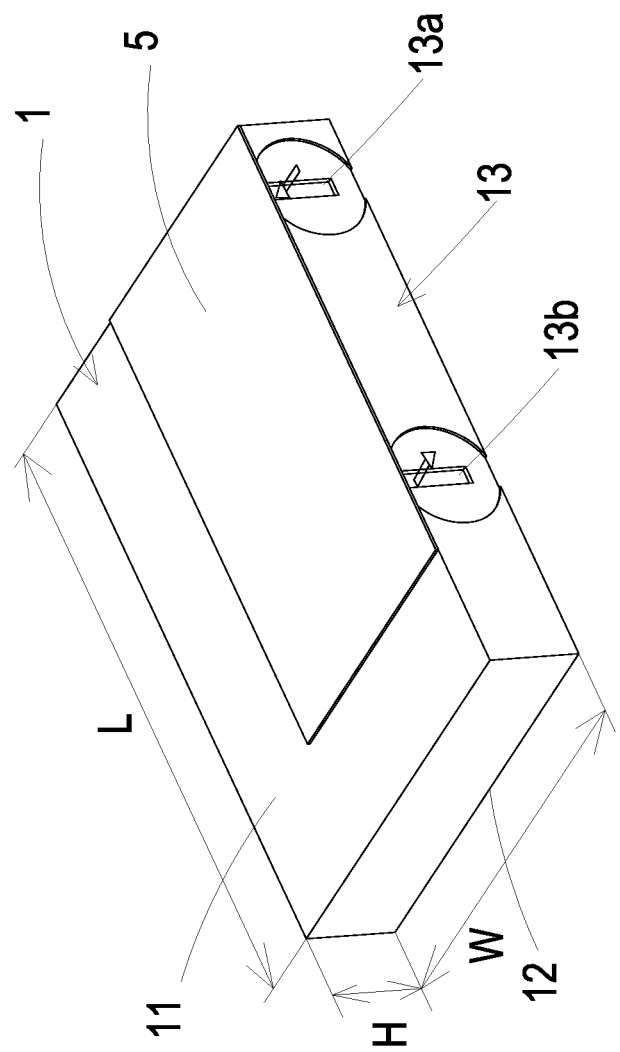
FIG. 1A is a schematic exterior view illustrating the gas detecting module of the present disclosure.
Figure 1B:
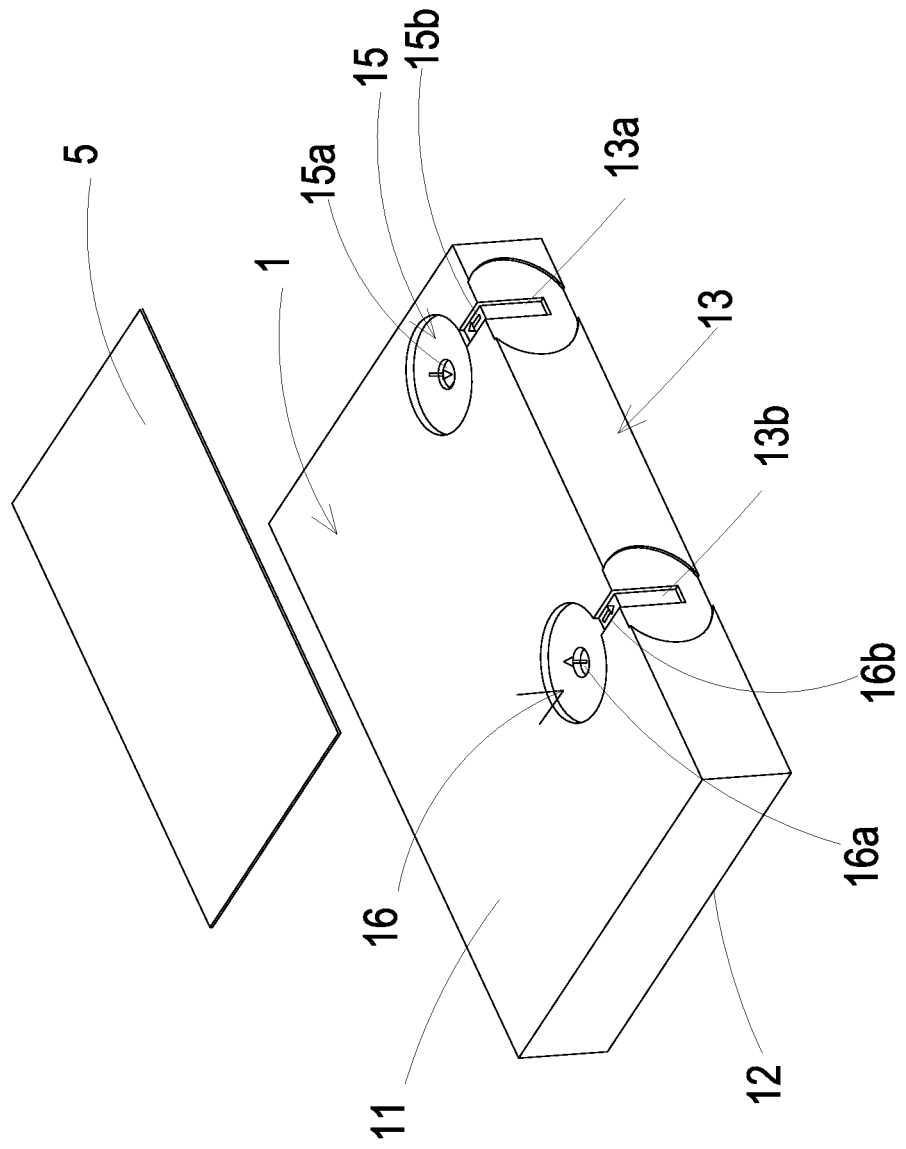
FIG. 1B is a schematic exploded view illustrating the position of the thin film covering the base of the gas detecting module.
Figure 1C:
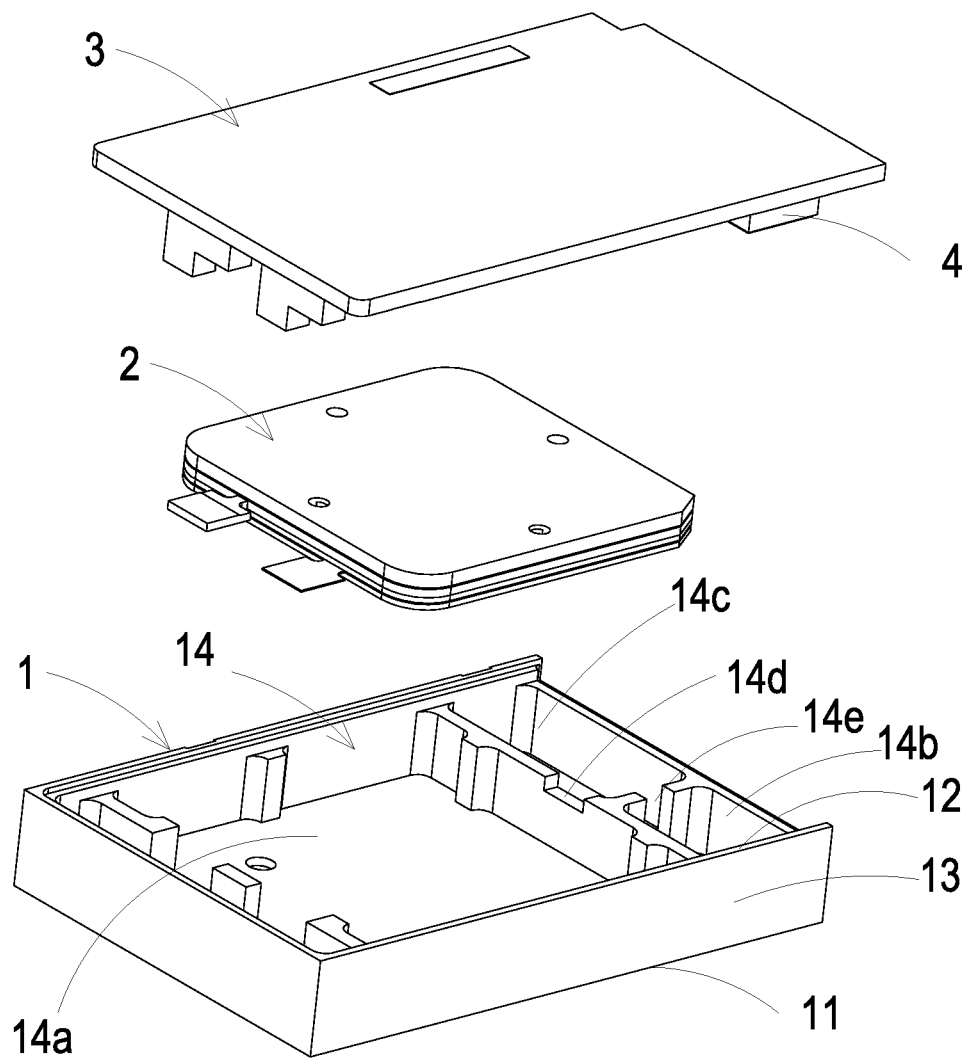
FIG. 1C is a schematic exploded view illustrating the associated components of the gas detecting module.

Please refer to FIG. 1A to 1C. The present disclosure provides a gas detecting module including a base 1, a micro pump 2, a driving circuit board 3, a gas sensor 4 and a thin film 5. The base 1 includes a first surface 11, a second surface 12, four sidewalls 13, an accommodating space 14, a gas-inlet-groove region 15 and a gas-outlet-groove region 16. The first surface 11 and the second surface 12 are two opposite surfaces. The four sidewalls 13 are extending longitudinally formed from the perimeter of the first surface 11 to the perimeter of the second surface 12. In the embodiment, one of the sidewalls 13 has a gas-inlet concave 13a and a gas-outlet concave 13b, which are recessed therefrom. The gas-inlet concave 13a and the gas-outlet concave 13b are spaced apart. The accommodating space 14 is recessed from the second surface 12 toward the first surface 11 and located in an inner space defined by the plurality of sidewalls 13. In the embodiment, the accommodating space 14 is divided into a micro-pump-loading region 14a, a detection region 14b and a gas-flowing-path region 14c. Preferably but not exclusively, the micro-pump-loading region 14a and the gas-flowing-path region 14c are in fluid communication with each other through a venting hole 14d. Preferably but not exclusively, the detection region 14b and the gas-flowing-path region 14c are in fluid communication with each other through a communicating opening 14e.

In the embodiment, the gas-inlet-groove region 15 is recessed on the first surface 11, and includes a gas-inlet aperture 15a and a gas-inlet groove 15b. The gas-inlet aperture 15a is in fluid communication with the gas-flowing-path region 14c. The gas-inlet groove 15b is connected between the gas-inlet aperture 15a and the gas-inlet concave 13a, so that the gas-inlet aperture 15a and the gas-inlet concave 13a are in fluid communication with each other.

In the embodiment, the gas-outlet-groove region 16 is recessed on the first surface 11, and includes a gas-outlet aperture 16a and a gas-outlet groove 16b. The gas-outlet aperture 16a is in fluid communication with the micro-pump-loading region 14a. The gas-outlet groove 16b is connected between the gas-outlet aperture 16a and the gas-outlet concave 13b, so that the gas-outlet aperture 16a and the gas-outlet concave 13b are in fluid communication with each other.

Figure 2:
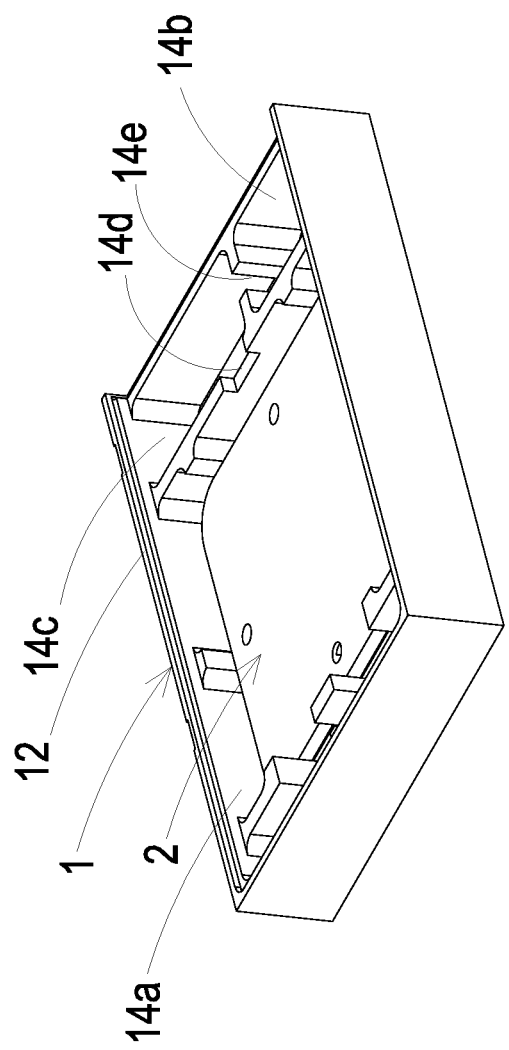
FIG. 2 is a schematic exterior view illustrating the micro pump assembled on the base of the gas detecting module

Please refer to FIG. 1C and FIG. 2. In the embodiment, the micro pump 2 is accommodated within the micro-pump-loading region 14a of the accommodating space 14 and covers the gas-outlet aperture 16a. In addition, the micro pump 2 is electrically connected to the driving circuit board 3. The actions of the micro pump 2 are controlled by a driving signal provided by the driving circuit board 3. The driving signal (not shown) for the micro pump 2 is provided by the driving circuit board 3.

Please further refer to FIG. 1C. In the embodiment, the driving circuit board 3 covers and is attached to the second surface 12 of the base 2 to form the micro-pump-loading region 14a, the detection region 14b and the gas-flowing-path region 14c of the accommodating space 14. In that, gas is inhaled through the gas-inlet aperture 15a of the gas-inlet-groove region 15, and discharged out through the gas-outlet aperture 16a of the gas-outlet-groove region 16 to form a gas flowing path.

In the embodiment, the gas sensor 4 is positioned and disposed on the driving circuit board 3, and electrically connected to the driving circuit board 3. When the driving circuit board 3 is attached to the second surface 12 of the base 1, the gas sensor 4 is accommodated correspondingly within the detection region 14b of the accommodating space 14 to detect the gas flowing therethrough and obtain gas information.

In the embodiment, the thin film 5 is attached to the first surface 11 of the base 1, and covers the gas-inlet-groove region 15 and the gas-outlet-groove region 16. In that, the gas is inhaled through the gas-inlet concave 13a of the sidewall 13, flows in the gas-inlet-groove region 15 through the gas-inlet groove 15b, and then flows into the gas flowing path through the gas-inlet aperture 15a, and is discharged out through the gas-outlet aperture 16a of the gas-outlet-groove region 16. Consequently, the gas is laterally discharged out the gas detecting module through the connection of the gas-outlet concave 13b of the sidewall 13 to the gas-outlet groove 16b.

From the above descriptions, the micro pump 2 accelerates the flow of the gas, and the gas outside the gas detecting module is laterally inhaled relative to the gas detecting module into the gas-flowing-path region 14c through the gas-outlet concave 13a of the sidewall 13, flows into the detection region 14b to be detected by the gas sensor 4 disposed therein, and is discharged out through the gas-outlet aperture 16a of the gas-outlet-groove region 16 by the micro pump 2, so that the gas is laterally discharged out the gas detecting module through the connection of the gas-outlet concave 13b of the sidewall 13 to the gas-outlet groove 16b. In the embodiment, the gas sensor 4 is a volatile-organic-compound (VOC) sensor. The present disclosure is not limited thereto. In other embodiments, the thin film 5 is not attached to the first surface 11 of the base 1. In that, the gas is inhaled into the gas flowing path through the gas-inlet aperture 15a, and discharged out through the gas-outlet aperture 16a of the gas-outlet-groove region 16 directly, so that the gas is vertically inhaled and discharged out relative to the gas detecting module. By using the gas detecting module of the present disclosure, the gas can be laterally inhaled and discharged out or vertically inhaled and discharged out the gas detecting module. The applications of the gas detecting module are adjustable according to the practical requirements and not redundantly described herein.

Figure 3:
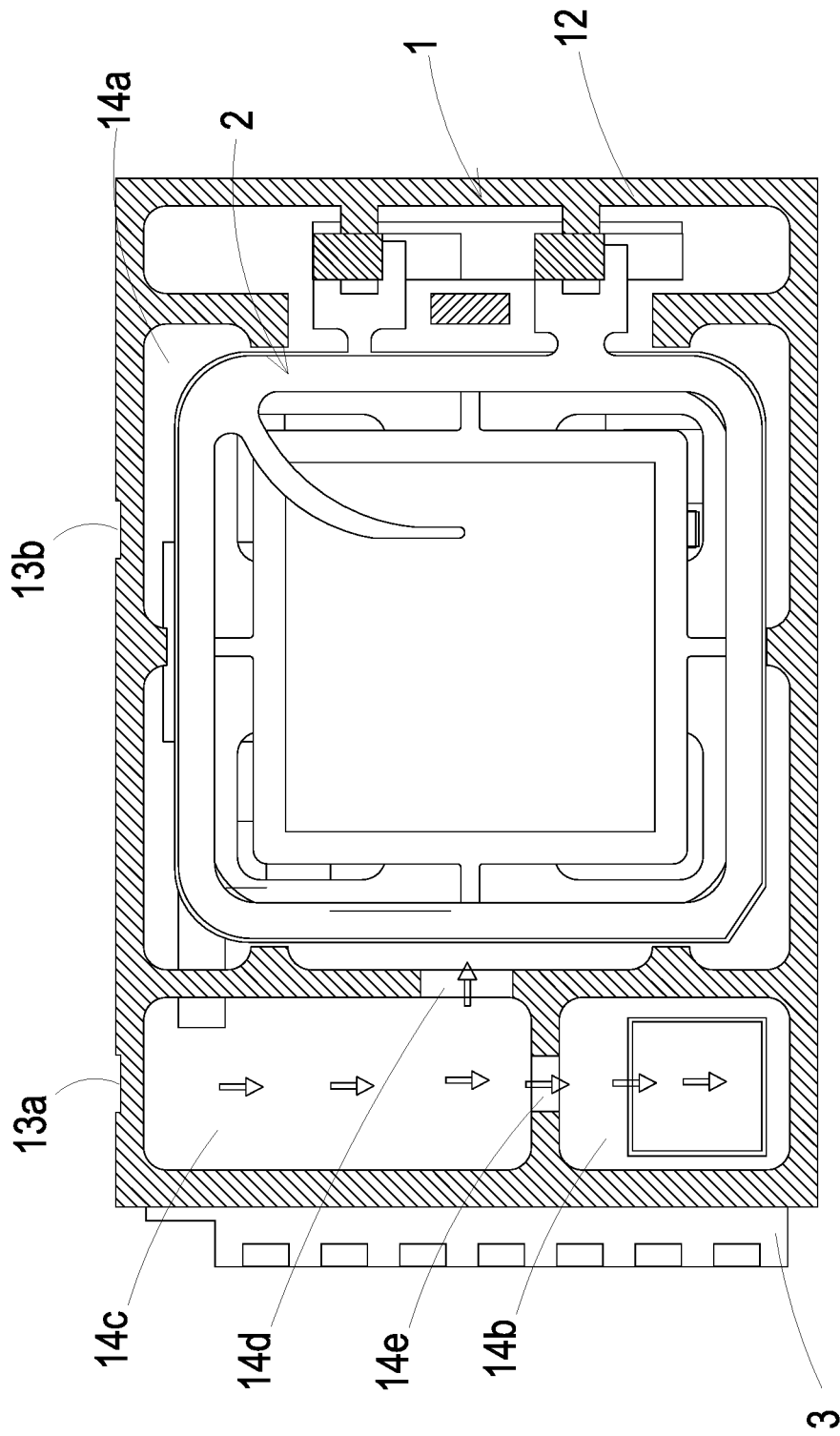
FIG. 3 is a schematic cross-sectional view illustrating a gas flowing path of the gas detecting module.
Figure 4:
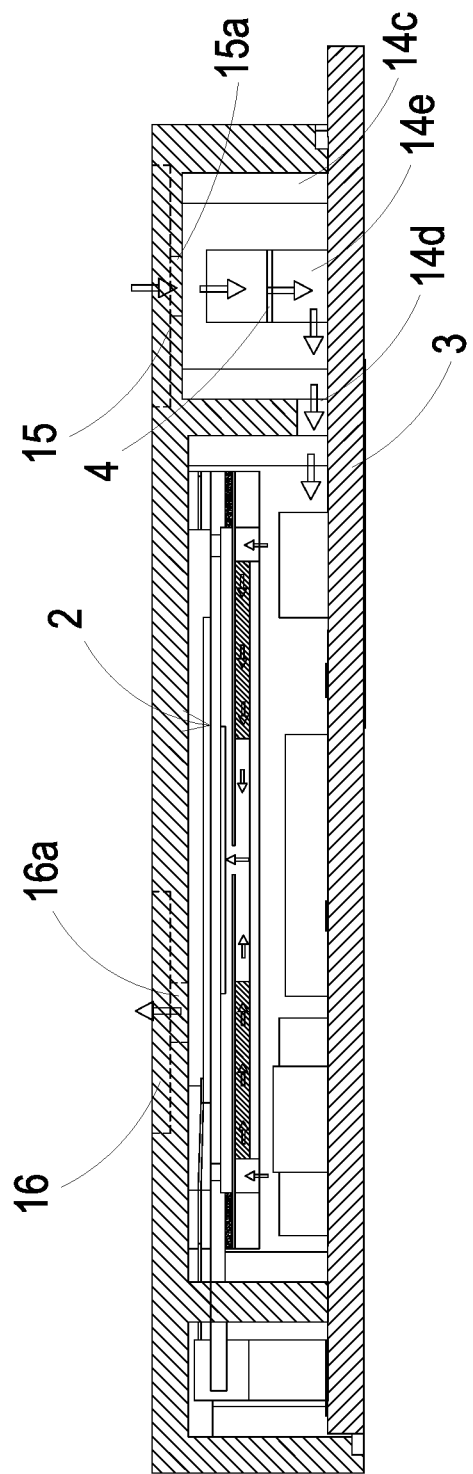
FIG. 4 is a schematic cross-sectional view illustrating a gas flowing path of the gas detecting module and taken from another perspective angle.

Please refer to FIGS. 3 and 4. In the embodiment, a driving signal is provided by the driving circuit board 3 to control the actions of the micro pump 2. When the micro pump 2 is enabled, the gas contained in the micro-pump-loading region 14a is inhaled and discharged out through the gas-outlet aperture 16a. At this time, a negative pressure is formed in the micro-pump-loading region 14a, so that the gas contained in the gas-flowing-path region 14c in fluid communication with the venting hole 14d flows into the micro-pump-loading region 14*a* through the venting hole 14*d*. Moreover, the gas is inhaled into the gas-flowing-path region 14*c* through the gas-inlet aperture 15*a* of the gas-inlet-groove region 15. In addition to the gas in the gas-flowing-path region 14*c* flowing into the micro-pump-loading region 14*a*, a part of the gas also flows into the detection region 14*b* through the communicating opening 14*e*, for the gas sensor 4 disposed in the detection region 14*b* to detect gas information.

Figure 5A:
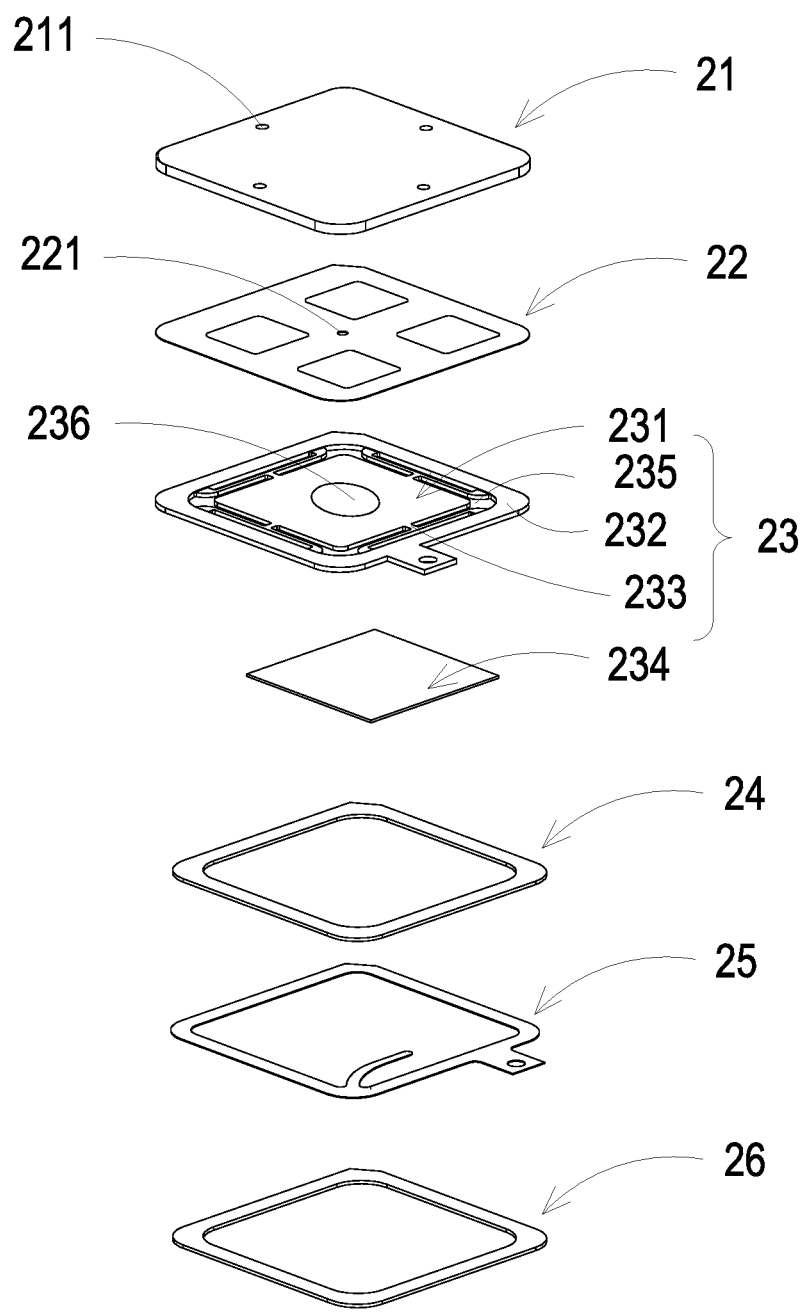
FIG. 5A is a schematic exploded view illustrating the micro pump of the gas detecting module.
Figure 5B:
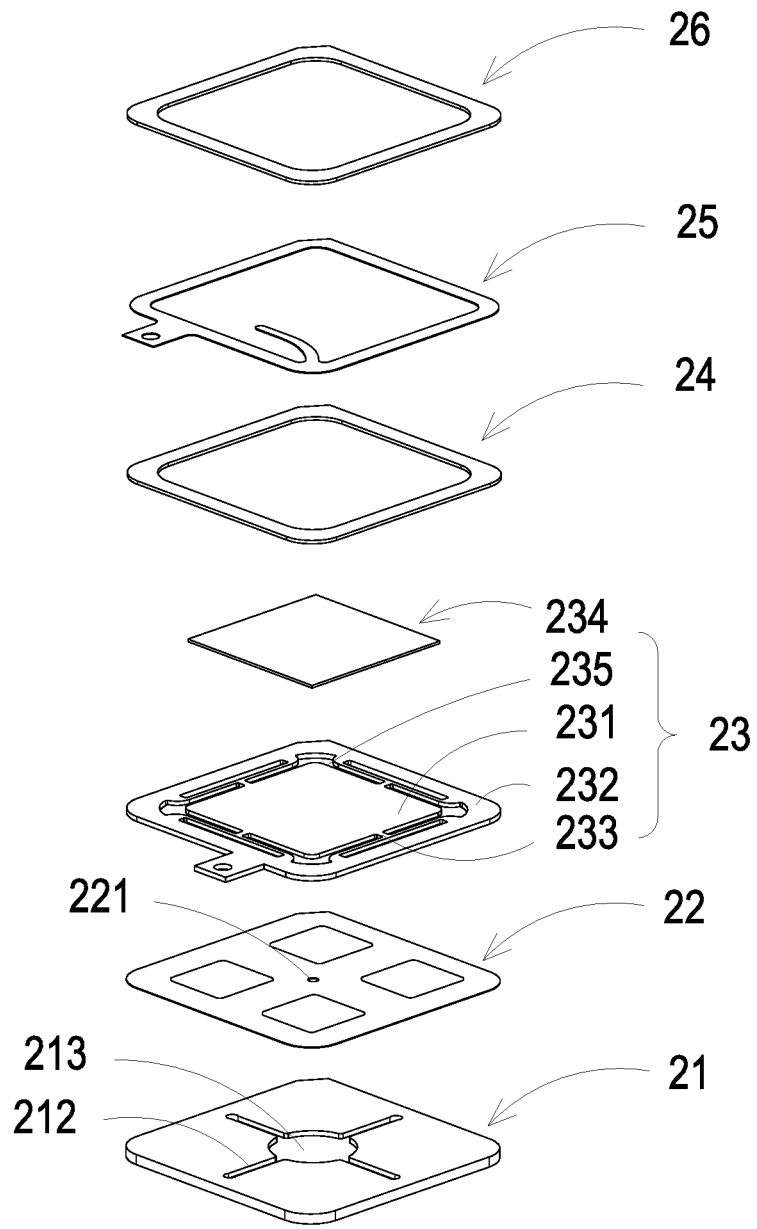
FIG. 5B is a schematic exploded view illustrating the micro pump of the gas detecting module and taken from another perspective angle.

Please refer to FIGS. 5A and 5B. In the embodiment, the micro pump 2 includes a gas-inlet plate 21, a resonance plate 22, a piezoelectric actuator 23, a first insulation plate 24, a conducting plate 25 and a second insulation plate 26. The piezoelectric actuator 23 spatially corresponds to the resonance plate 22. In the embodiment, the gas-inlet plate 21, the resonance plate 22, the piezoelectric actuator 23, the first insulation plate 24, the conducting plate 25 and the second insulation plate 26 are sequentially stacked on each other.

Figure 6A:
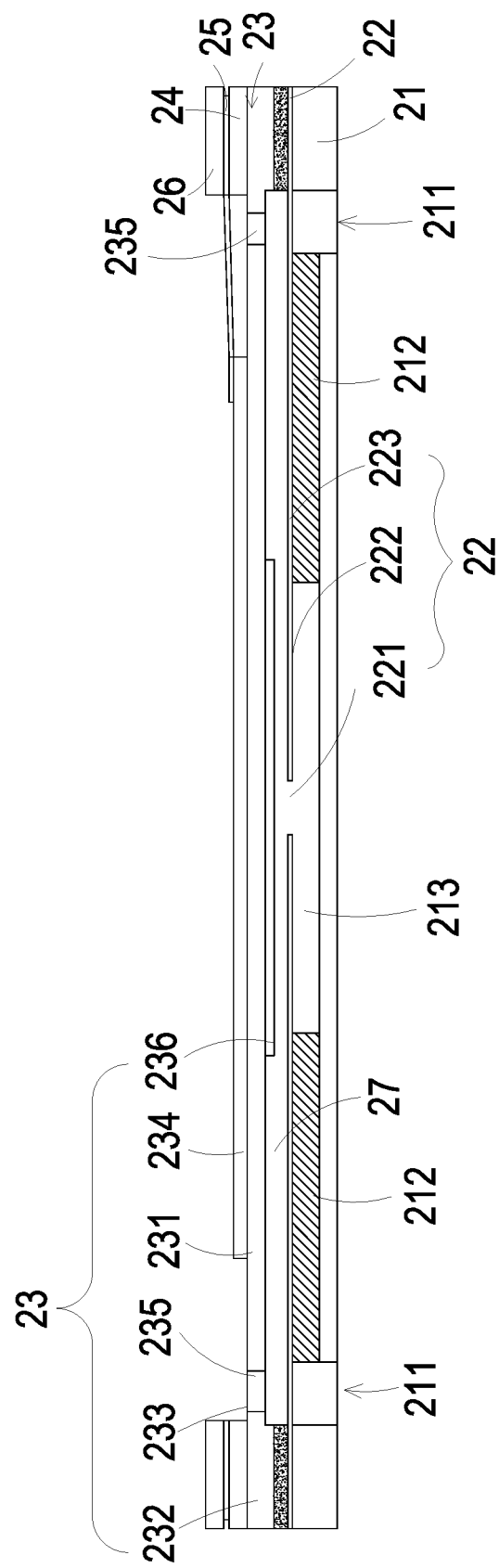
FIG. 6A is a schematic cross-sectional view illustrating the micro pump of the gas detecting module.
Figure 6B:
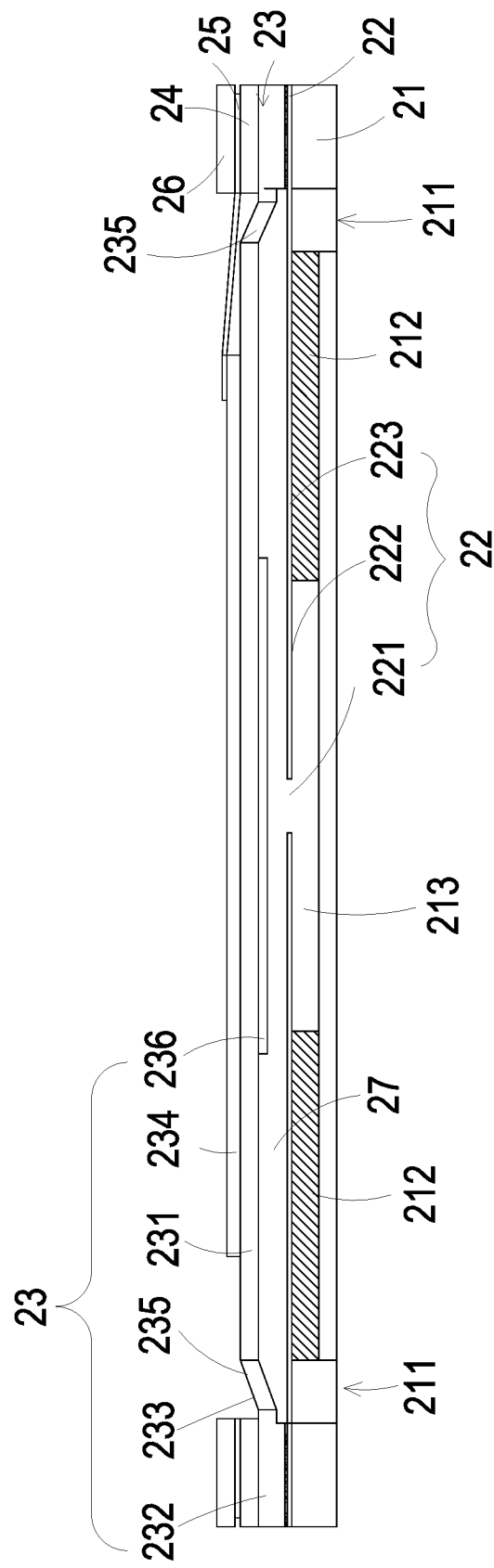
FIG. 6B is a schematic cross-sectional view illustrating the micro pump of the gas detecting module according to another embodiment.
Figure 6C:
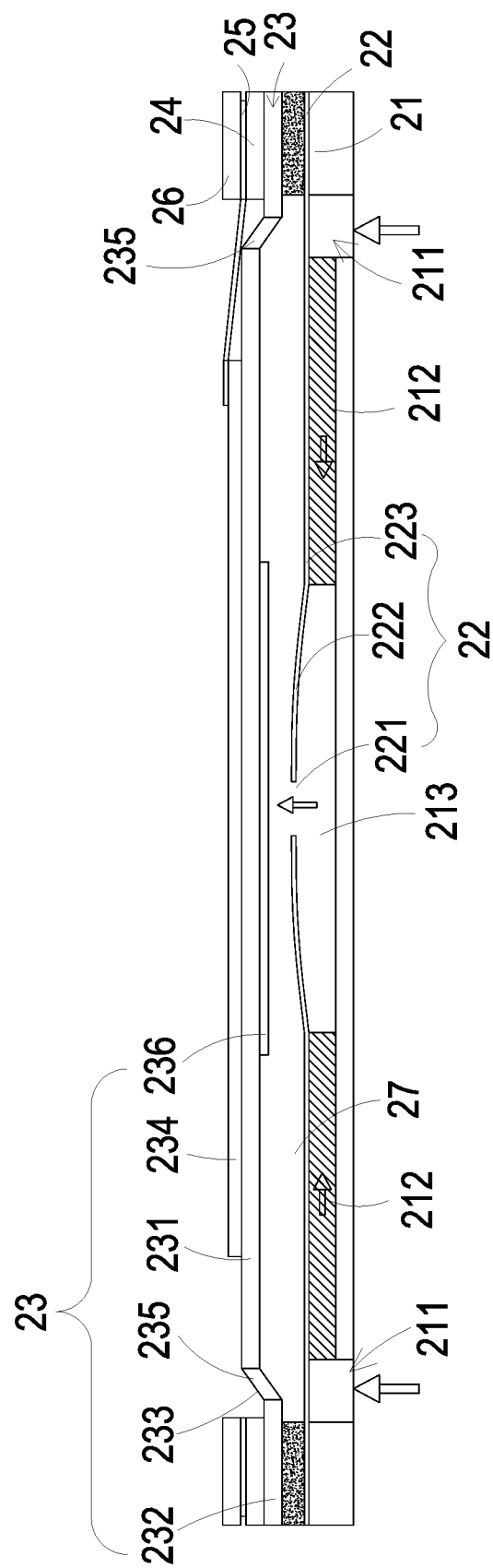
FIG. 6C to 6E schematically illustrate the actions of the micro pump in FIG. 6A.

Please refer to FIGS. 5A and 5B and FIG. 6C. In the embodiment, the gas-inlet plate 21 includes at least one inlet aperture 211, at least one convergence groove 212 and a convergence chamber 213. Preferably but not exclusively, there are four inlet apertures 211. The present disclosure is not limited thereto. The inlet aperture 211 passes through the gas-inlet plate 21 to allow the gas to flow into the micro pump 2 in response to the effect of atmospheric pressure. In the embodiment, the gas-inlet plate 21 includes the at least one convergence groove 212. The number and the arrangement of the convergence grooves 212 correspond to the inlet apertures 211 disposed on another surface. Preferably but not exclusively, there are four inlet apertures 211 and four convergence grooves 212 spatially corresponding with each other. In the embodiment, the convergence chamber 213 is located at a center of the gas-inlet plate 21. Each convergence groove 212 has an end in fluid communication to the inlet aperture 211 corresponding thereto, and another end in fluid communication to the convergence chamber 213 located at the center of the gas-inlet plate 21. Thus, the gas inhaled into the convergence grooves 212 through the inlet aperture 211 is transported and converged into the convergence chamber 213. Preferably but not exclusively, the inlet apertures 211, the convergence grooves 212 and the convergence chamber 213 of the gas-inlet plate 21 are integrally formed into one piece. In some embodiments, the gas-inlet plate 21 is made of stainless steel, but limited thereto. In other embodiments, the depth of the convergence chamber 213 is the same as the depth of the convergence groove 212, but not limited thereto.

In the embodiment, the resonance plate 22 is made by a flexible material, but not limited thereto. The resonance plate 22 has a central aperture 221, which is aligned with the convergence chamber 213 of the gas-inlet plate 21, to allow the gas to flow therethrough. The resonance plate 22 has a movable part 222, and the movable part 222 surrounds the central aperture 221. In some embodiments, the resonance plate 22 is made by a copper material, but not limited thereto.

In the embodiment, the piezoelectric actuator 23 is collaboratively formed and assembled by a suspension plate 231, an outer frame 232, at least one bracket 233 and a piezoelectric element 234. The suspension plate 231 is a square shape and permitted to undergo a bending deformation. The outer frame 232 is disposed around the suspension plate 231. The at least one bracket 233 is connected between the suspension plate 231 and the outer frame 232 for elastically supporting the suspension plate 231. The piezoelectric element 234 is a square shape and attached to a first surface of the suspension plate 231. When a voltage is applied to the piezoelectric element 234, the suspension plate 231 is driven to undergo the bending deformation. Preferably but not exclusively, a length of a side of the piezoelectric element 234 is smaller than or equal to a length of a side of the suspension plate 231. A plurality of vacant spaces 235 are formed among the suspension plate 231, the outer frame 232 and the bracket 233. In addition, the piezoelectric actuator 23 further includes a bulge 236 disposed on a second surface of the suspension plate 231, so that the bulge 236 and the piezoelectric element 234 are disposed on two opposite surfaces of the suspension plate 231. When the piezoelectric actuator 23 is enabled, the gas is inhaled from the inlet aperture 211 of the gas-inlet plate 21, converged in the convergence chamber 213 through the convergence groove 212, and passes through the central aperture 221 of the resonance plate 22, whereby the gas is further transferred through a resonance between the piezoelectric actuator 23 and the movable part 222 of the resonance plate 22.

As shown in FIG. 6A, the gas-inlet plate 21, the resonance plate 22, the piezoelectric actuator 23, the first insulation plate 24, the conducting plate 25 and the second insulation plate 26 are sequentially stacked on each other. The thickness of the suspension plate 231 of the piezoelectric actuator 23 is smaller than the thickness of the outer frame 232. When the resonance plate 22 is stacked on the piezoelectric actuator 23, a chamber space 27 is formed among the suspension plate 231 and the outer frame 232 of the piezoelectric actuator 23 and the resonance plate 22.

Please refer to FIG. 6B. A micro pump 2 according to another embodiment has the similar structures, elements and configurations as those of the above embodiment (FIG. 6A) and is not redundantly described herein. Different from the above embodiment, the suspension plate 231 of the piezoelectric actuator 23 is formed by stamping and extended away from the resonance plate 22, so that the suspension plate 231 and the outer frame 232 are not at the same height level. While the gas-inlet plate 21, the resonance plate 22, the piezoelectric actuator 23, the first insulation plate 24, the conducting plate 25 and the second insulation plate 26 are sequentially stacked, a chamber distance is formed between a surface of the suspension plate 231 and the resonance plate 22. The transportation efficiency of the micro pump 2 is influenced by the chamber distance, so that it is very important to maintain the chamber distance fixed for the micro pump 2 to provide a stable transportation efficiency. In this way, the suspension plate 231 of the micro pump 2 is produced by stamping, so as to make it recessed. Thus, a surface of the suspension plate 231 and a surface of the outer frame 232 are collaborated to form a non-coplanar structure. Namely, the surface of the suspension plate 231 and the surface of the outer frame 232 are non-coplanar, and a stepped structure is formed. The surface of the suspension plate 231 is spaced apart from the surface of the outer frame 232. In that, the suspension plate 231 of the piezoelectric actuator 23 is recessed to form a space corresponding to the resonance plate 22, so that the space is collaborated with the resonance plate 231 to make the chamber distance adjustable. The structure of the suspension plate 231 of the piezoelectric actuator 23 is directly modified to form a chamber space by stamping. In this way, the required chamber distance is achieved by adjusting the recessed distance of the suspension plate 231 of the piezoelectric actuator 23. Thus, the adjustment of the chamber distance is simplified in the structural design. Moreover, the advantages of simplifying the manufacturing process and saving the manufacturing time are achieved.

Figure 6D:
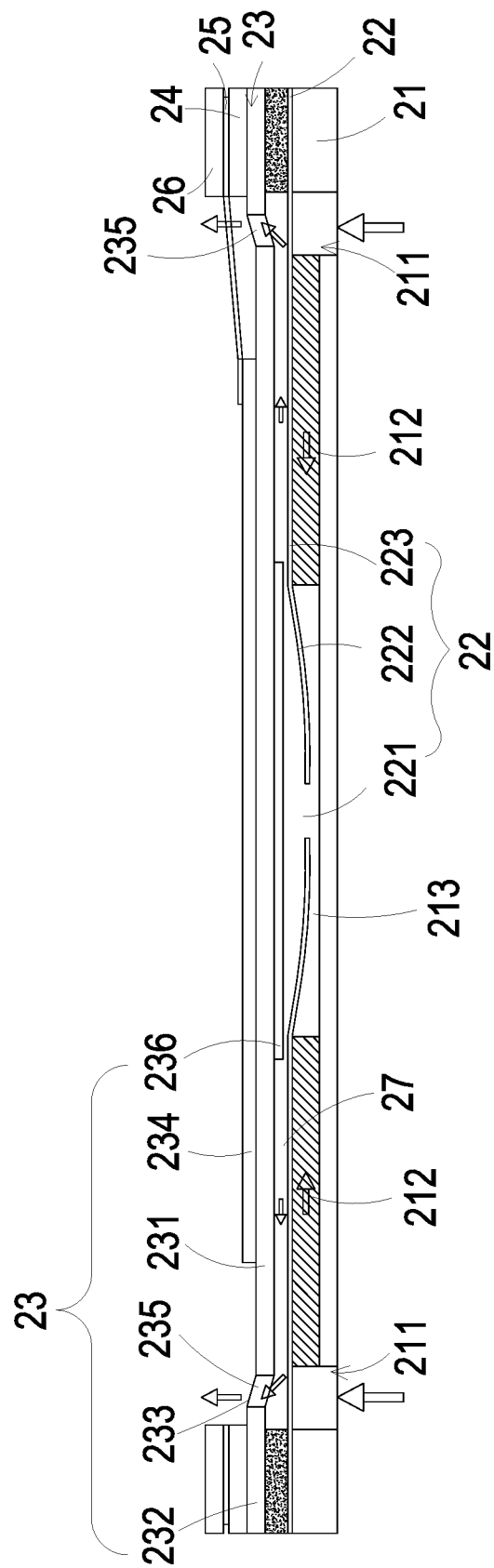
Figure 6E:
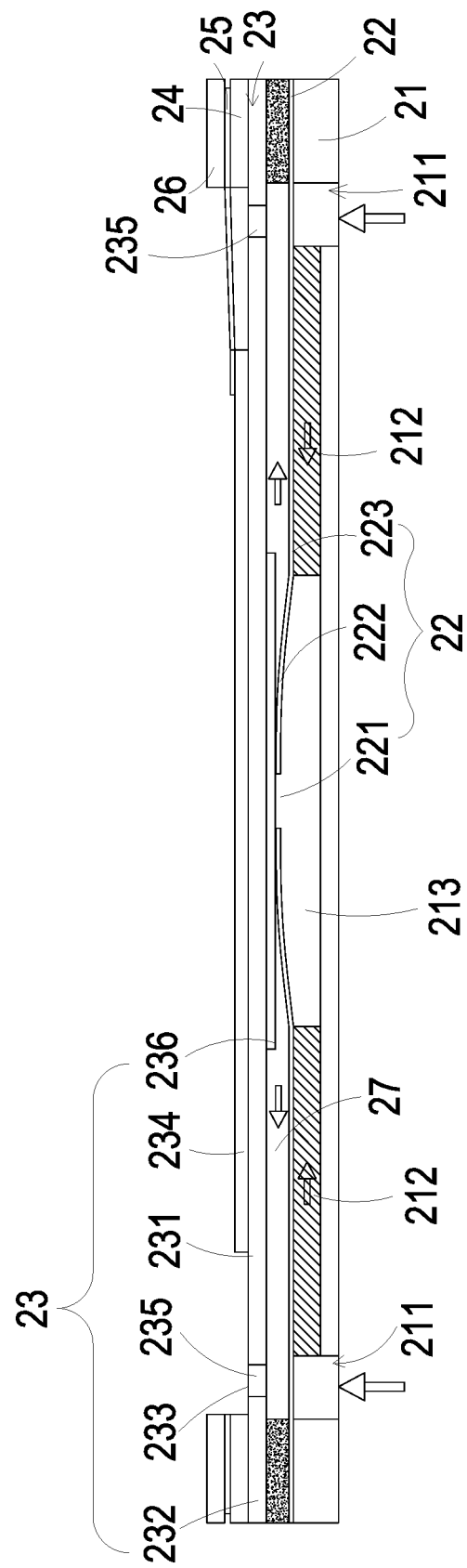

In order to describe the actions of gas transportation in the above-mentioned micro pump 2, please refer to FIGS. 6C to 6E. Firstly, please refer to FIG. 6C. When a driving voltage is applied to the piezoelectric element 234 of the piezoelectric actuator 23, the suspension plate 231 is driven to undergo the bending deformation and move upwardly. In that, the volume of the chamber space 27 is expended rapidly, the internal pressure of the chamber space 27 is decreased to form a negative pressure, and the gas contained in the convergence chamber 213 is inhaled and enters the chamber space 27. At the same time, the resonance plate 22 is synchronously driven to move upwardly under the influence of the resonance principle, and the volume of the convergence chamber 213 is expended. Since the gas contained the convergence chamber 213 enters the chamber space 27, it results that the convergence chamber 213 is also under a negative pressure. Consequently, the gas is inhaled into the convergence chamber 213 through the inlet aperture 211 and the convergence groove 212. Please refer to FIG. 6D. When the piezoelectric element 234 drives the suspension plate 231 to move downwardly, the chamber space 27 is compressed. Similarly, the suspension plate 231 drives the resonance plate 22 to move downwardly due to the resonance, and the gas in the chamber space 27 is compressed to move downwardly and further transported upwardly through vacant spaces 235. Consequently, the gas is discharged out of the micro pump 2. Finally, please refer to FIG. 6E. When the suspension plate 231 is moved back to the original position, the resonance plate 22 is further moved downwardly due to the principle of inertia. At this time, the gas contained in the chamber space 27 is compressed by the resonance plate 22 and moved toward the vacant spaces 235, and the volume of the convergence chamber 213 is expended. Consequently, the gas is continuously transported through the inlet apertures 211 and the convergence grooves 212 and converged in the convergence chamber 213. By repeating the above actions shown in FIGS. 6C to 6E, the gas is inhaled from the inlet aperture 211 and flows into a flow channel formed by the gas-inlet plate 21 and the resonance plate 22 to generate a pressure gradient, and then the gas is transported upwardly through the vacant spaces 235 to achieve the gas transportation at high speed. The effect of gas transportation of the micro pump 2 is achieved.

Figure 7A:
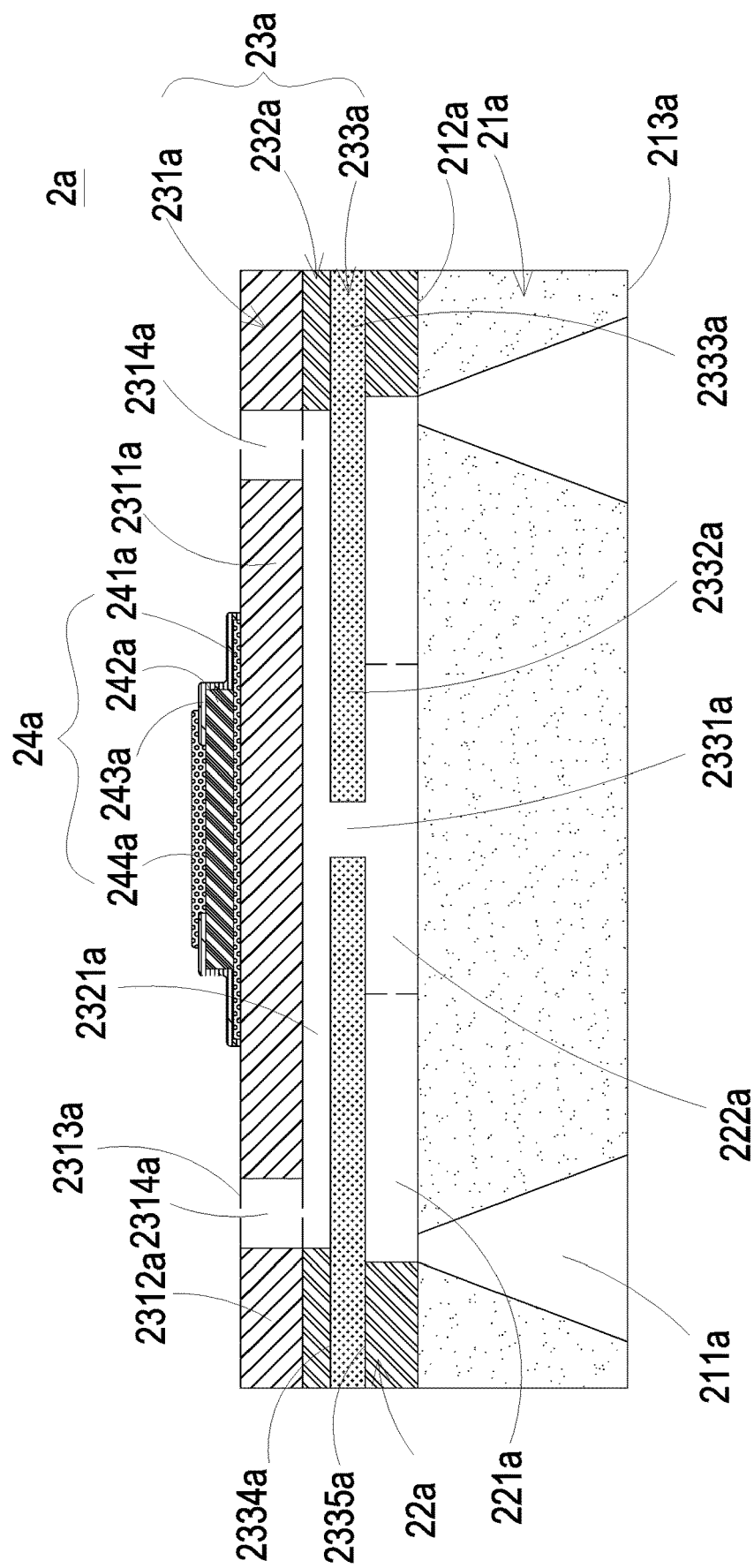
FIG. 7A is a schematic cross-sectional view illustrating the MEMS pump.
Figure 7B:
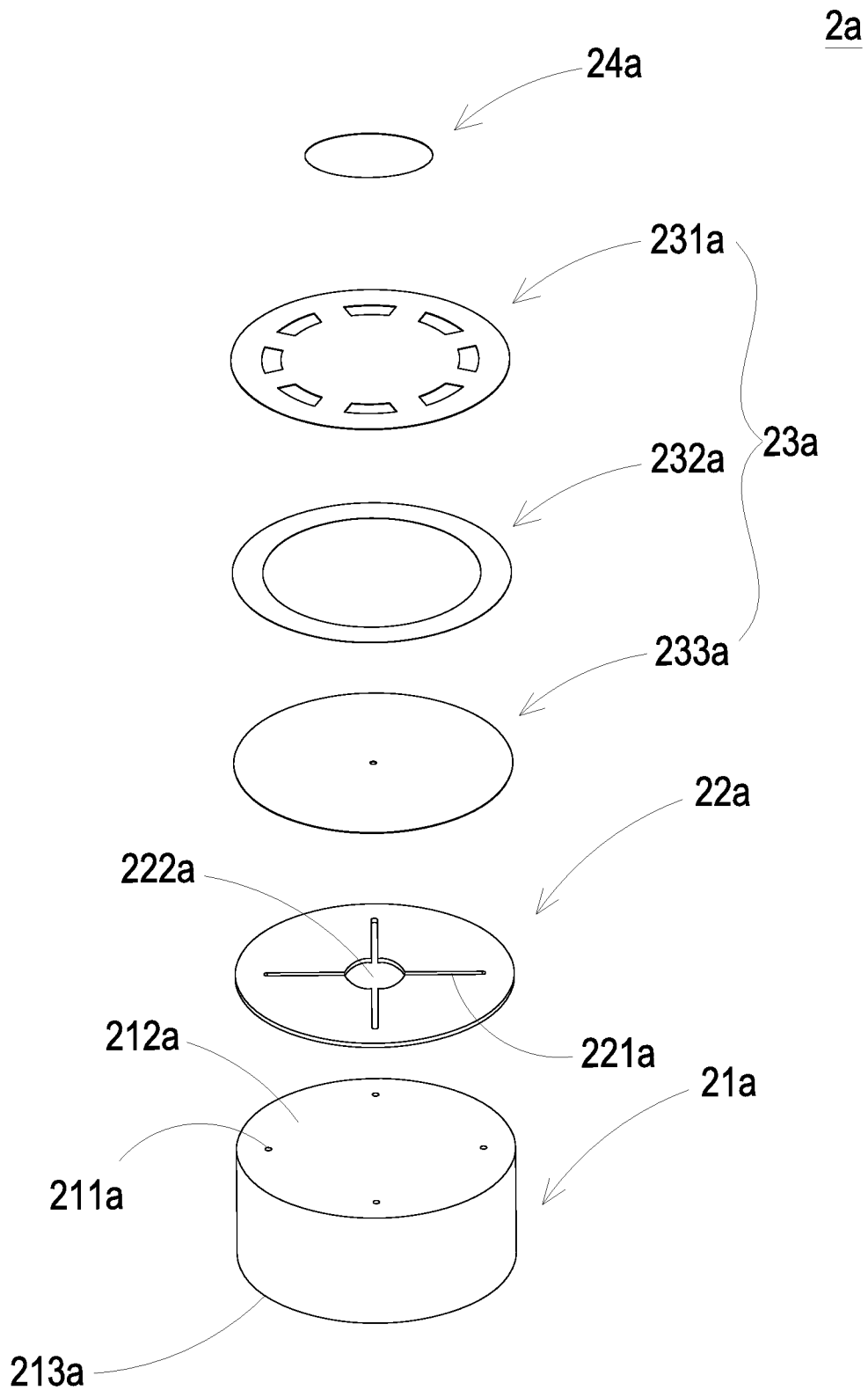
FIG. 7B is a schematic exploded view illustrating the MEMS pump.

The micro pump 2 in the above embodiment can be replaced with a microelectromechanical systems (MEMS) pump 2a in another embodiment. Please refer to FIG. 7A and FIG. 7B. The MEMS pump 2a includes a first substrate 21a, a first oxidation layer 22a, a second substrate 23a and a piezoelectric component 24a. In addition, the MEMS pump 2a of the present disclosure is produced by the semiconductor manufacturing process, such as epitaxy, deposition, lithography and etching in. The structure is disassembled. In order to detail show its internal structure, an exploded view is used to describe it.

In the embodiment, the first substrate 21a is a Si wafer and has a thickness ranging from 150 μm to 400 μm. The first substrate 21a includes a plurality of inlet apertures 211a, a first surface 212a and a second surface 213a. In the embodiment, there are four inlet apertures 211a, but the present disclosure is not limited thereto. Each inlet aperture 211a penetrates from the second surface 213a to the first surface 212a. In order to improve the inlet-inflow effect, the plurality of inlet apertures 211a are tapered-shaped, and the size is decreased from the second surface 213a to the first surface 212a.

The first oxidation layer 22a is a silicon dioxide ($SiO_2$) thin film and has the thickness ranging from 10 μm to 20 μm. The first oxidation layer 22a is stacked on the first surface 212a of the first substrate 21a. The first oxidation layer 22a includes a plurality of convergence channels 221a and a convergence chamber 222a. The numbers and the arrangements of the convergence channels 221a and the inlet apertures 211a of the first substrate 21a are corresponding with each other. In the embodiment, there are four convergence channels 221a. First ends of the four convergence channels 221a are in fluid communication with the four inlet apertures 211a of the first substrate 21a, and second ends of the four convergence channels 221a are in fluid communication with the convergence chamber 222a. Thus, after the gas is inhaled through the inlet apertures 211a, the gas flows through the corresponding convergence channels 221a and is converged into the convergence chamber 222a.

In the embodiment, the second substrate 23a is a silicon on insulator (SOI) wafer, and includes a silicon wafer layer 231a, a second oxidization layer 232a and a silicon material layer 233a. The silicon wafer layer 231a has a thickness ranging from 10 μm to 20 μm, and includes an actuating portion 2311a, an outer peripheral portion 2312a, a plurality of connecting portions 2313a and a plurality of fluid channels 2314a. The actuating portion 2311a is in a circular shape. The outer peripheral portion 2312a is in a hollow ring shape and disposed around the actuating portion 2311a. The plurality of connecting portions 2313a are connected between the actuating portion 2311a and the outer peripheral portion 2312a, respectively, so as to connect the actuating portion 2311a and the outer peripheral portion 2312a for elastically supporting. The plurality of fluid channels 2314a are disposed around the actuating portion 2311a and located between the connecting portions 2313a.

The second oxidation layer 232a is a silicon monoxide (SiO) layer and has a thickness ranging from 0.5 μm to 2 μm. The second oxidation layer 232a is formed on the silicon wafer layer 231a and in a hollow ring shape. A vibration chamber 2321a is collaboratively defined by the second oxidation layer 232a and the silicon wafer layer 231a. The silicon material layer 233a is in a circular shape, disposed on the second oxidation layer 232a and bonded to the first oxide layer 22a. The silicon material layer 233a is a silicon dioxide ($SiO_2$) thin film and has a thickness ranging from 2 μm to 5 μm. In the embodiment, the silicon material layer 223a includes a through hole 2331a, a vibration portion 2332a, a fixing portion 2333a, a third surface 2334a and a fourth surface 2335a. The through hole 2331a is formed at a center of the silicon material layer 233a. The vibration portion 2332a is disposed around the through hole 2331a and vertically corresponds to the vibration chamber 2321a. The fixing portion 2333a is disposed around the vibration portion 2332a and located at a peripheral region of the silicon material layer 233a. The silicon material layer 233a is fixed on the second oxidation layer 232a through the fixing portion 2333a. The third surface 2334a is connected to the second oxidation layer 232a. The fourth surface 2335a is connected to the first oxidation layer 22a. The piezoelectric component 24a is stacked on the actuating portion 2311a of the silicon wafer layer 231a.

The piezoelectric component 24a includes a lower electrode layer 241a, a piezoelectric layer 242a, an insulation layer 243a and an upper electrode layer 244a. The lower electrode 241a is stacked on the actuating portion 2311a of the silicon wafer layer 231a. The piezoelectric layer 242a is stacked on the lower electrode layer 241a. The piezoelectric layer 242a and the lower electrode layer 241a are electrically connected through the contact area thereof. In addition, the width of the piezoelectric layer 242a is less than the width of the lower electrode layer 241a, so that the lower electrode layer 241a is not completely covered by the piezoelectric layer 242a. The insulation layer 243a is stacked on a partial surface of the piezoelectric layer 242a and a partial surface of the lower electrode layer 241a, which is uncovered by the piezoelectric layer 242a. The upper electrode layer 244a is stacked on the insulation layer 243a and a remaining surface of the piezoelectric layer 242a without the insulation layer 243a disposed thereon, so that the upper electrode layer 244a is contacted and electrically connected with the piezoelectric layer 242a. At the same time, the insulation layer 243a is used for insulation between the upper electrode layer 244a and the lower electrode layer 241a, so as to avoid the short circuit caused by direct contact between the upper electrode layer 244a and the lower electrode layer 241a.

Figure 8A:
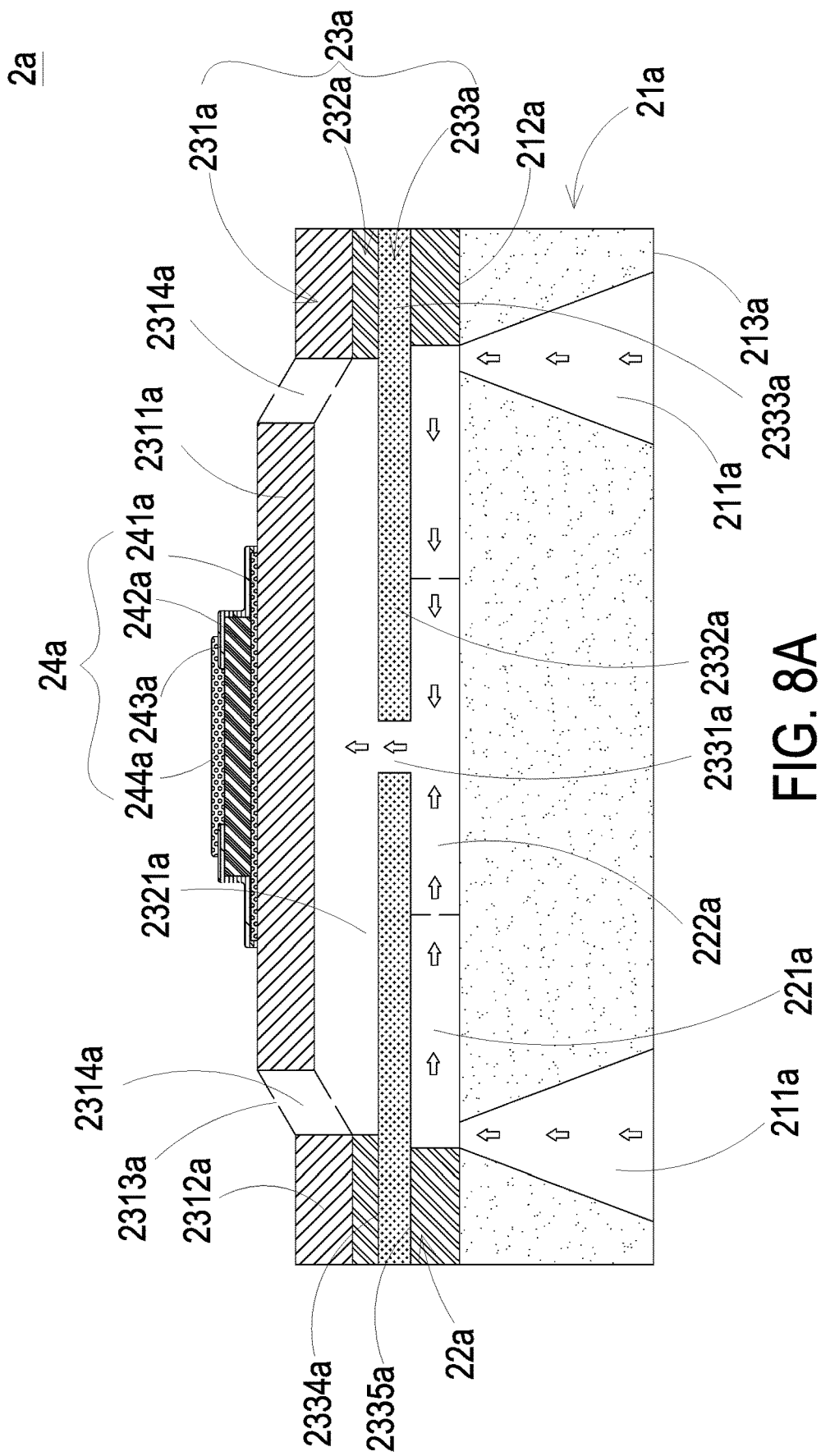
FIG. 8A to 8C schematically illustrate the actions of the MEMS pump.
Figure 8B:
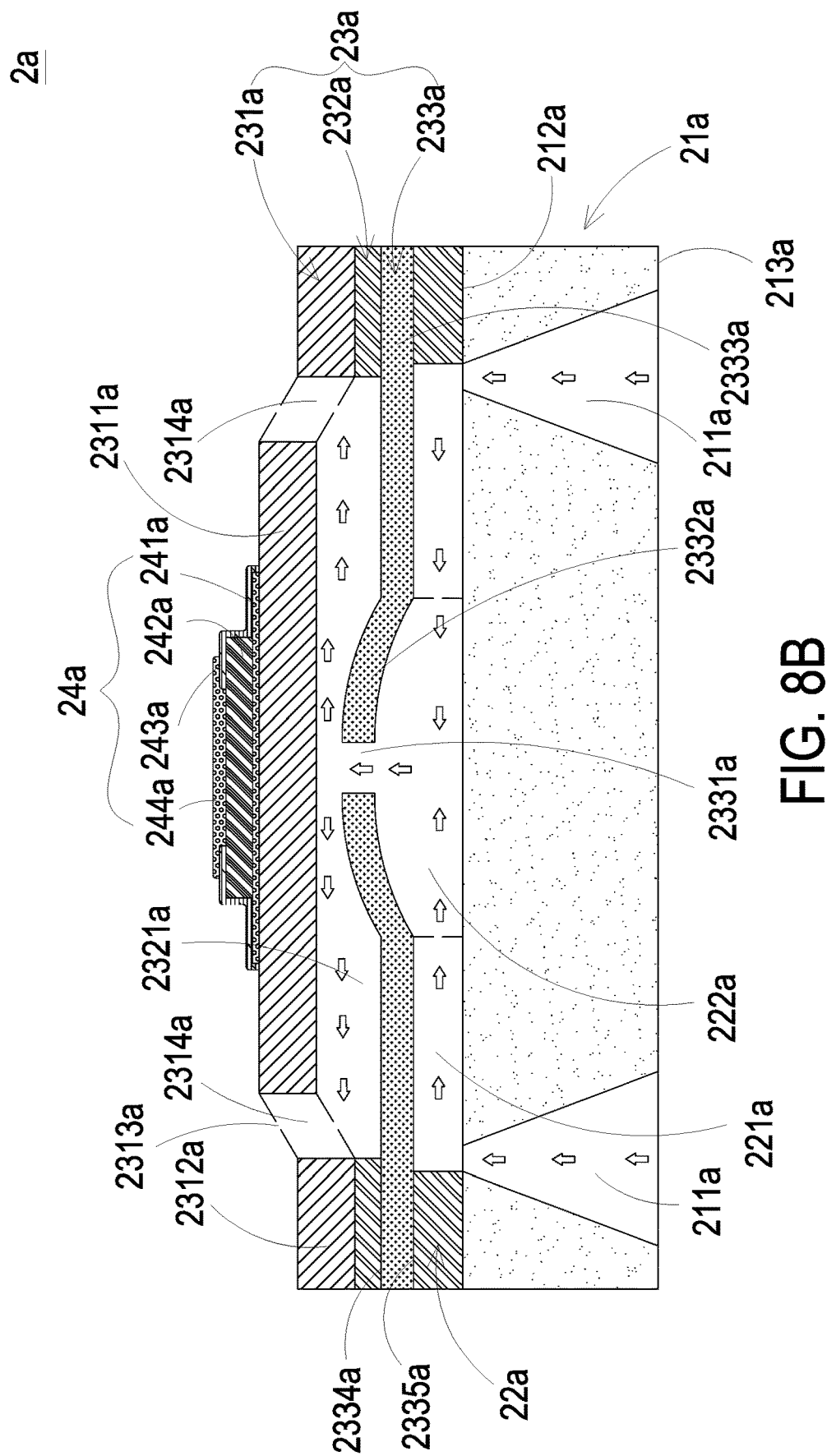
Figure 8C:
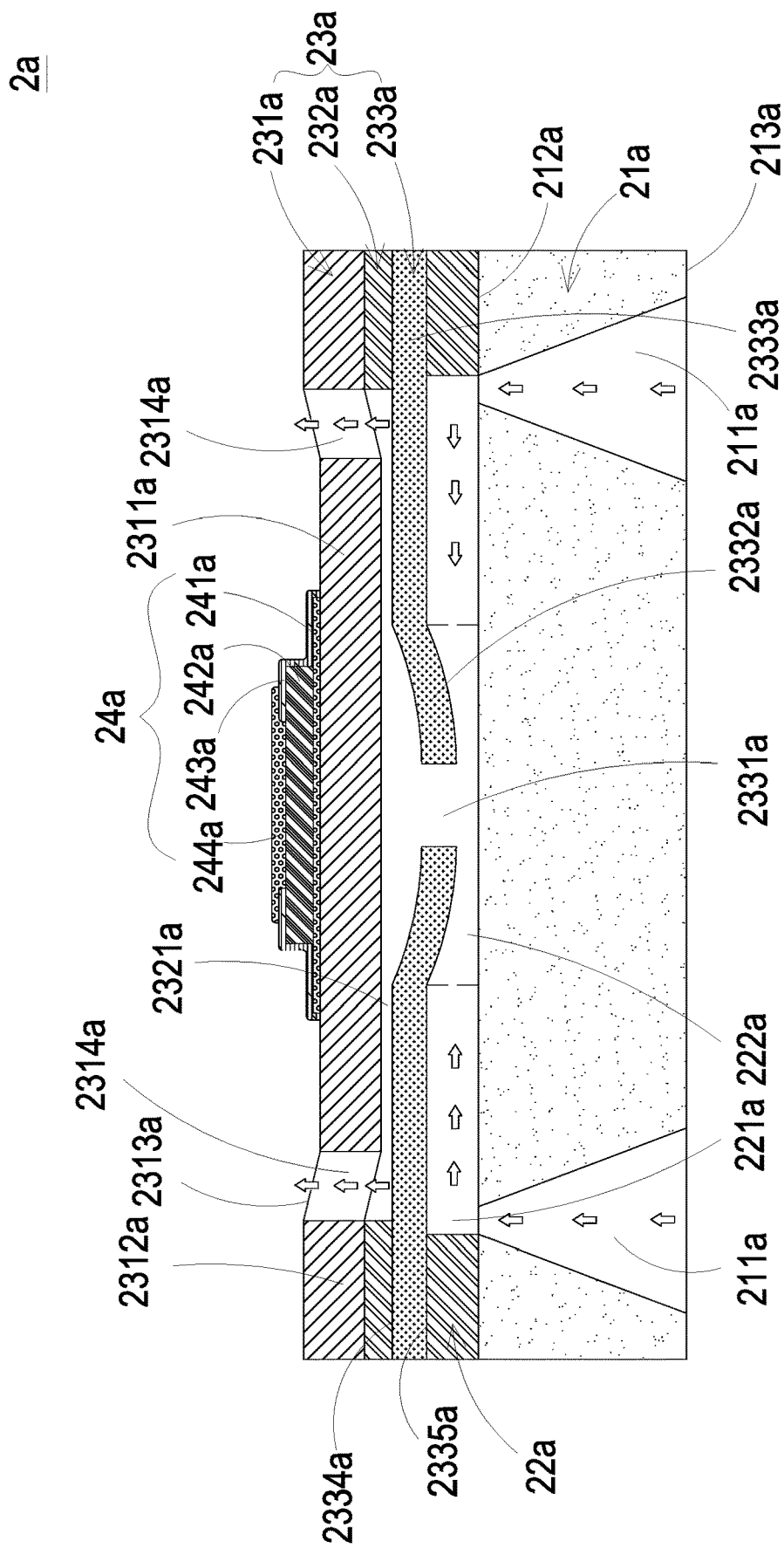

Please refer to FIGS. 8A to 8C. FIGS. 8A to 8C schematically illustrate the actions of the MEMS pump. As shown in FIG. 8A, a driving voltage and a driving signal (not shown) transmitted from the driving circuit board 3 are received by the lower electrode layer 241a and the upper electrode layer 244a of the piezoelectric component 24a, and further transmitted to the piezoelectric layer 242a. After the piezoelectric layer 242a receives the driving voltage and the driving signal, the deformation of the piezoelectric layer 242a is generated due to the influence of the reverse piezoelectric effect. In that, the actuating portion 2311a of the silicon wafer layer 231a is driven to displace. When the piezoelectric component 24a drives the actuating portion 2311a to move upwardly, the actuating portion 2311a is separated away from the second oxidation layer 232a to increase the distance therebetween. In that, the volume of the vibration chamber 2321a of the second oxidation layer 232a is expended rapidly, the internal pressure of the vibration chamber 2321a is decreased to form a negative pressure, and the gas in the convergence chamber 222a of the first oxidation layer 22a is inhaled into the vibration chamber 2321a through the through hole 2331a. Further as shown in FIG. 8B, when the actuating portion 2311a is driven by the piezoelectric component 24a to move upwardly, the vibration portion 2332a of the silicon material layer 233a is moved upwardly due to the influence of the resonance principle. When the vibration portion 2332a is moved upwardly, the space of the vibration chamber 2321a is compressed and the gas in the vibration chamber 2321a is pushed to move to the fluid channels 2314a of the silicon wafer layer 231a. In that, the gas flows upwardly through the fluid channel 2314a and is discharged out. Moreover, when the vibration portion 2332a is displaced upwardly to compress the vibration chamber 2321a, the volume of the convergence chamber 222a is expended due to the displacement of the vibration portion 2332a, the internal pressure of the convergence chamber 222a is decreased to form a negative pressure, and the gas outside the MEMS pump 2a is inhaled into the convergence chamber 222a through the inlet apertures 211a. As shown in FIG. 8C, when the piezoelectric component 24a is enabled to drive the actuating portion 2311a of the silicon wafer layer 231a to displace downwardly, the gas in the vibration chamber 2321a is pushed to flow to the fluid channels 2314a, and is discharged out. At the same time, the vibration portion 2332a of the silicon material layer 233a is driven by the actuating portion 2311a to displace downwardly, and the gas in the convergence chamber 222a is compressed to flow to the vibration chamber 2321a through the through hole 2331a. Thereafter, when the piezoelectric component 24a drives the actuating portion 2311a to displace upwardly, the volume of the vibration chamber 2321a is greatly increased, and then there is a higher suction force to inhale the gas into the vibration chamber 2321a. By repeating the above actions, the actuating portion 2311a is continuously driven by the piezoelectric element 24a to displace upwardly and downwardly, and further to drive the vibration portion 2332a to displace upwardly and downwardly. By changing the internal pressure of the MEMS pump 2a, the gas is inhaled and discharged continuously, thereby achieving the actions of the MEMS pump 2a.

Figure 9:
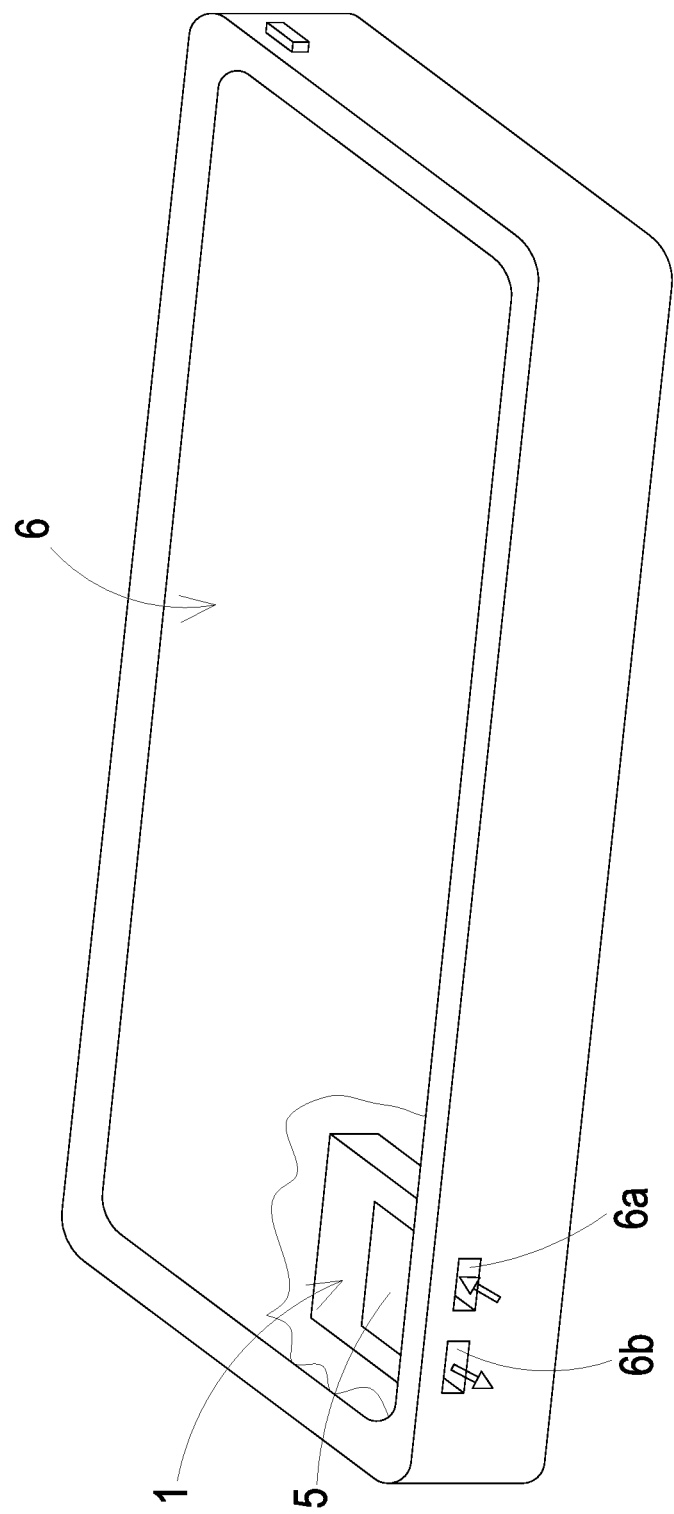
FIG. 9 is a schematic perspective view illustrating the gas detecting module embedded in a mobile device.
Figure 10:
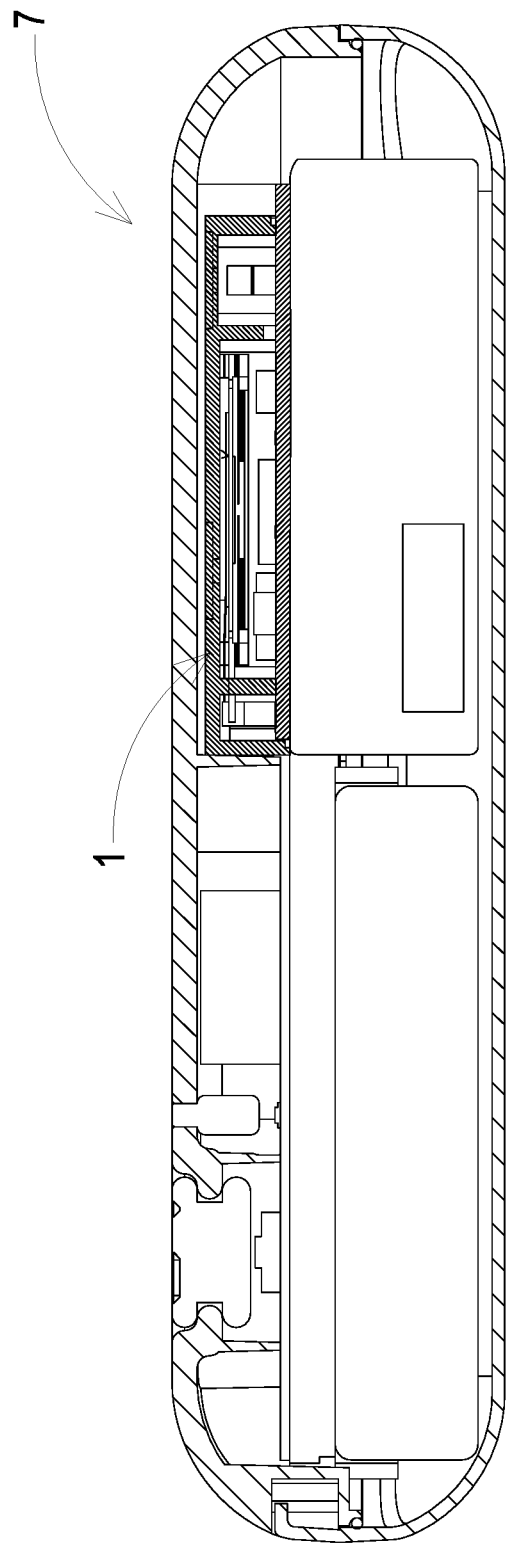
FIG. 10 is a schematic cross-sectional view illustrating the gas detecting module embedded in a portable electronic device.

Please refer to FIG. 1A and FIG. 9. The gas flowing path of the gas detecting module of the present disclosure is designed to have a lateral inlet and a lateral outlet, so as to facilitate the gas detecting module to be embedded in a mobile device 6 for application. Moreover, it is beneficial of minimizing the overall structural design of the gas detecting module. The length L of the gas detecting module is reduced to range from 2 mm to 4 mm, the width W of the gas detecting module is reduced to range from 2 mm to 4 mm, and the thickness H of the gas detecting module is reduced to range from 1 mm to 3.5 mm. More specifically, by using the MEMS pump 2a as a gas transporting device, the length L of the gas detecting module is further reduced to range from 2 mm to 3 mm, the width W of the gas detecting module is further reduced to range from 2 mm to 3 mm, and the thickness H of the gas detecting module is further reduced to range from 1 mm to 2.5 mm. While the gas detecting module is applied to the mobile device 6, the lateral inlet and the lateral outlet of the gas detecting module are matched to the gas inlet 6a and gas outlet 6b disposed on the lateral sidewall of the mobile device 6, so that the gas detecting module of the present disclosure can be easily embedded in the mobile device 6 for application. Preferably but not exclusively, the mobile device 6 is a smart phone or a smart watch. Please refer to FIG. 10. The gas detecting module is assembled within a portable electronic device 7. Preferably but not exclusively, the portable electronic device 7 is one selected from the group consisting of a mobile power supply, an air-quality-detection device and an air purifier.

From the above descriptions, the present disclosure provides a gas detecting module. In the gas detecting module, the gas-inlet concave and the gas-outlet concave are recessed on the sidewall of the base, the gas-inlet-groove region and the gas-outlet-groove region are recessed on the first surface of the base, the gas-inlet concave is in fluid communication with the gas-inlet-groove region, the gas-outlet concave is in fluid communication with the gas-outlet-groove region, and the thin film covers and seals the gas-inlet-groove region and the gas-outlet-groove region. In that, the effect of transporting the gas through the lateral inlet and the lateral outlet is achieved. Moreover, the micro pump is used to transport the gas. The base, the micro pump, the driving circuit board and the gas sensor of the present disclosure are assembled to form the gas detecting module. The length L of the gas detecting module is reduced to range from 2 mm to 3 mm, the width W of the gas detecting module is reduced to range from 2 mm to 3 mm, and the thickness H of the gas detecting module is reduced to range from 1 mm to 2.5 mm. It facilitates the gas detecting module to be embedded in a mobile device or a portable electronic device easily and matched with it. The present disclosure includes the industrial applicability and the inventive steps.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A gas detecting module, comprising:
   a base comprising:
      a first surface;
      a second surface opposite to the first surface;
      a plurality of sidewalls extending longitudinally from the perimeter of the first surface to the perimeter of the second surface, wherein one of the sidewalls has a gas-inlet concave and a gas-outlet concave recessed therefrom, and the gas-inlet concave and the gas-outlet concave are spaced apart;
      an accommodating space recessed from the second surface toward the first surface and located in an inner space defined by the plurality of sidewalls, wherein the accommodating space is divided into a micro-pump-loading region, a detection region and a gas-flowing-path region, wherein the micro-pump-loading region and the gas-flowing-path region are in communication with each other through a venting hole, and the detection region and the gas-flowing-path region are in communication with each other through a communicating opening;
      a gas-inlet-groove region recessed on the first surface and comprising a gas-inlet aperture and a gas-inlet groove, wherein the gas-inlet aperture is in communication with the gas-flowing-path region, and the gas-inlet groove is in communication with the gas-inlet concave of the sidewall; and
      a gas-outlet-groove region recessed on the first surface and comprising a gas-outlet aperture and a gas-outlet groove, wherein the gas-outlet aperture is in communication with the micro-pump-loading region, and the gas-outlet groove is in communication with the gas-outlet concave of the sidewall;
   a micro pump accommodated within the micro-pump-loading region and covering the gas-outlet aperture;
   a driving circuit board covering and attached to the second surface of the base to form the micro-pump-loading region, the detection region, and the gas-flowing-path region of the accommodating space, wherein gas is inhaled through the gas-inlet aperture of the gas-inlet-groove region and discharged out through the gas-outlet aperture of the gas-outlet-groove region to form a gas flowing path;
   a gas sensor disposed on and electrically connected to the driving circuit board and accommodated within the detection region to detect the gas flowing therethrough; and
   a thin film covering and attached to the gas-inlet-groove region and the gas-outlet-groove region, wherein the gas is laterally inhaled through the gas-inlet concave of the sidewall, flows into the gas-inlet-groove region through the gas-inlet groove, then flows into the gas flowing path through the gas-inlet aperture, and is discharged out through the gas-outlet aperture of the gas-outlet-groove region, so that the gas is laterally discharged out the gas detecting module through the connection of the gas-outlet concave of the sidewall to the gas-outlet groove;
   wherein a length of the gas detecting module ranges from 2 mm to 4 mm, a width of the gas detecting module ranges from 2 mm to 4 mm, and a thickness of the gas detecting module ranges from 1 mm to 3.5 mm, wherein the micro pump accelerates the flow of the gas, and the gas is laterally inhaled relative to the gas detecting module into the gas-flowing-path region through the gas-inlet concave of the sidewall, flows into the detection region to be detected, and is discharged out through the gas-outlet aperture of the gas-outlet-groove region by the micro pump, so that the gas is laterally discharged out the gas detecting module through the connection of the gas-outlet concave of the sidewall to the gas-outlet groove.

2. The gas detecting module according to claim 1, wherein the gas sensor is a volatile-organic-compound sensor.

3. The gas detecting module according to claim 1, wherein the length of the gas detecting module ranges from 2 mm to 3 mm, the width of the gas detecting module ranges from 2 mm to 3 mm, and the thickness of the gas detecting module ranges from 1 mm to 2.5 mm, wherein the micro pump is a microelectromechanical systems (MEMS) pump comprising:
   a first substrate having a plurality of inlet apertures, wherein the plurality of inlet apertures are tapered-shaped;
   a first oxidation layer stacked on the first substrate, wherein the first oxidation layer comprises a plurality of convergence channels and a convergence chamber, and the plurality of convergence channels are in communication between the convergence chamber and the plurality of inlet apertures;
   a second substrate combined with the first substrate and comprising:
      a silicon wafer layer, having:
         an actuating portion being in a circular shape;
         an outer peripheral portion being in a hollow ring shape and disposed around the actuating portion;
         a plurality of connecting portions connected between the actuating portion and the outer peripheral portion, respectively; and
         a plurality of fluid channels disposed around the actuating portion and located between the connecting portions;
      a second oxidation layer formed on the silicon wafer layer and being in a hollow ring shape, wherein a vibration chamber is collaboratively defined by the second oxidation layer and the silicon wafer layer; and
      a silicon material layer being in a circular shape, disposed on the second oxidation layer and bonded to the first oxide layer, having:
         a through hole formed at a center of the silicon material layer;
         a vibration portion disposed around the through hole; and
         a fixing portion disposed around the vibration portion; and
      a piezoelectric component being in a circular shape and stacked on the actuating portion of the silicon wafer layer.

4. The gas detecting module according to claim 3, wherein the piezoelectric component comprises:
   a lower electrode layer;
   a piezoelectric layer stacked on the lower electrode layer;
   an insulation layer stacked on a partial surface of piezoelectric layer and a partial surface of the lower electrode layer; and an upper electrode layer stacked on the insulation layer and a remaining surface of the piezoelectric layer without the insulation layer disposed thereon, so as to electrically connect with piezoelectric layer.

\* \* \* \* \*